Nov. 6, 1973
W. H. JESSEL, JR., ET AL
Plant Pat. 3,405
CHRYSANTHEMUM PLANT
Filed Sept. 30, 1971
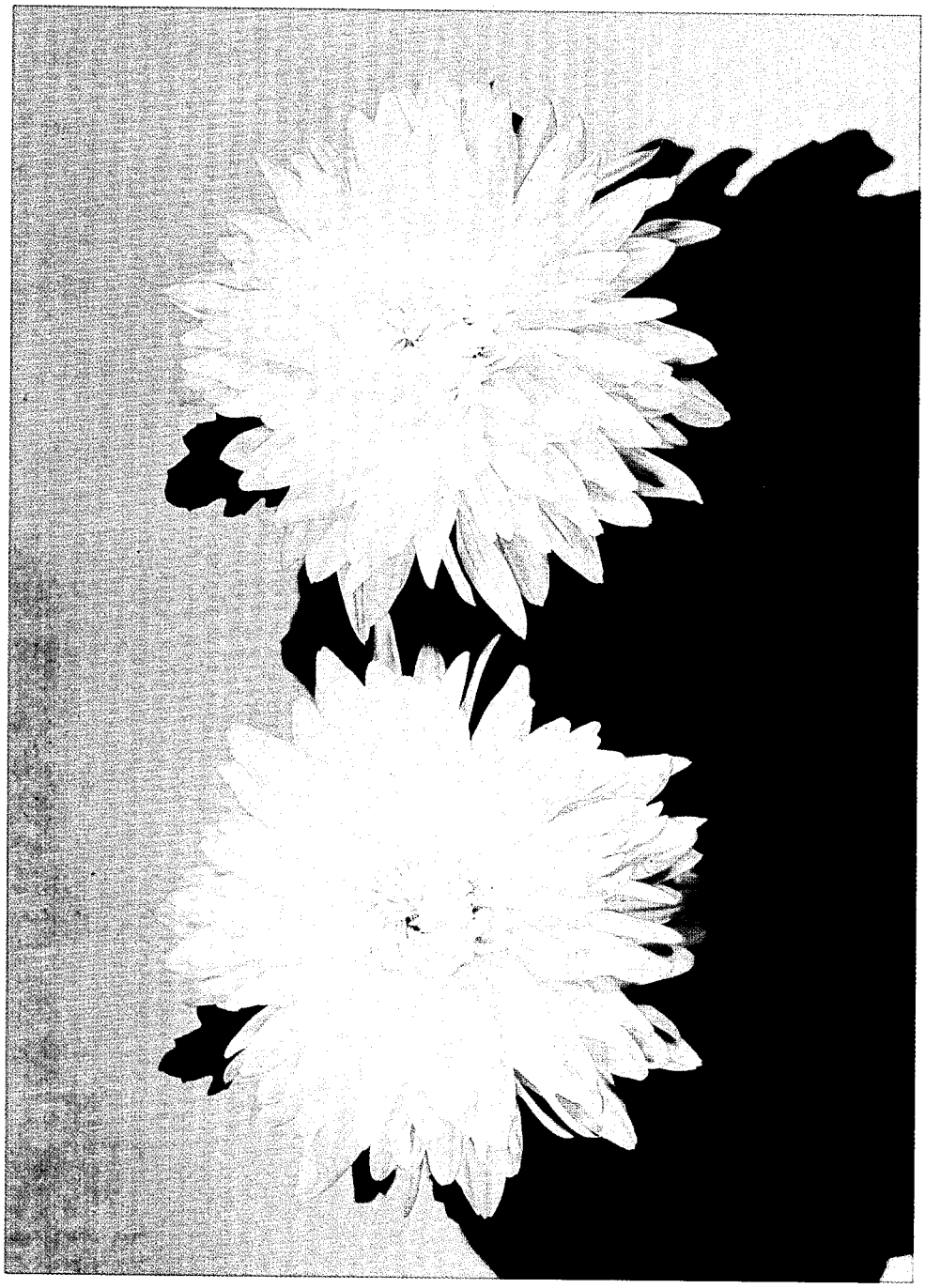

United States Patent Office

Plant Pat. 3,405

Patented Nov. 6, 1973

3,405
CHRYSANTHEMUM PLANT

Walter H. Jessel, Jr., Doylestown, and William E. Duffett, Akron, Ohio, assignors to Yoder Brothers, Inc., Barberton, Ohio

Filed Sept. 30, 1971, Ser. No. 185,459
Int. Cl. A01h *5/00*
U.S. Cl. Plt.—78 1 Claim

The present invention comprises a new and distinct cultivar of chrysanthemum plant which is a sport of the cultivar Paragon, disclosed and illustrated in our pending application for U.S. Plant Pat. Ser. No. 185,458, filed Sept. 30, 1971.

The new cultivar is similar in many respects to Paragon, having the same characteristics of:

(1) Flowering period.
(2) Plant habit.
(3) General flower form.

The new cultivar is distinguished from Paragon by the following characteristics when grown under comparable conditions:

(1) Its yellow flower color.
(2) A petal count approximately 15% to 25% greater. This contributes to a more highly crowned flower (greater depth) which is more pronounced in the high light periods of the year. Such higher crown results in a slight reflexing of the outer petals as the flower matures.
(3) Consistently responds at least two days ahead of Paragon.

The new cultivar was selected from a flowering block of the parent cultivar at Barberton, Ohio, and when asexually reproduced by cuttings at Barberton, Ohio, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Its optimum flowering periods for the various geographical areas is as follows: In the northern and western United States, from October through May; south and southwestern United States, November through early May; coastal California, January through December, and in Florida, November through early May.

The accompanying photographic drawing shows the unique characteristics of the new cultivar, the color being as nearly true as possible with color illustrations of this type. In the comparison photograph, the new cultivar appears on the left and the cultivar Paragon on the right.

In the description which follows, color references are made to the Munsel Color Book, 1963 edition, and comparisons are made with the parent cultivar Paragon. Where only a single value or description appears for the new cultivar, the same value or description applies also to the parent cultivar Paragon.

Botanical classification: *Chrysanthemum morifolium*

| | Yellow Paragon | Paragon |
|---|---|---|
| Bloom: | | |
| Size | 4½" | |
| Fully expanded | 5½" | |
| Borne | Terminal on disbudded stems | |
| Stems | Strong | |
| Form | Decorative | |
| Permanence | 12–16 days | |
| Color: | | |
| Center of flower | Yellow green, 2.5GY9/4 | Yellow green, 5GY9/2. |
| Base of petals | Yellow green, 5GY8/6 | Yellow green, 5GY8/6. |
| Inside of petals | Yellow, 10Y9/6 | White, N9.5/. |
| Reverse of petals | Yellow, 10Y9/4 | Do. |
| Tonality from a distance | Yellow, 10Y9/6 | Do. |
| Discoloration | do | Do. |
| Petals: | | |
| Texture | Smooth | |
| Appearance and form | Closed at base, broadening to a wide shallow keel, tapering to a blunt point with recurved petal edges. | |
| Arrangement | Composite, whorled on a single receptacle | |
| Persistence | Resists shatter | |
| Fragrance | Typical chrysanthemum | |
| Reproductive organs: | | |
| Stamen, anthers | None | |
| Pollen | do | |
| Arrangement | Clustered in center of flower, if present | |
| Styles | Present ray florets | |
| Length | Short | |
| Ovaries | At the base of petal attached to receptacle | |
| Planrt: | | |
| Form | Herbaceous | |
| Growth | Spreading | |
| Height | Approximately 12" when given 8-9 week medium treatment as outlined in timetables of Yoder Brothers, Inc., Barberton, Ohio. | |
| Spread | Approximately 8½" when given 8-9 week medium treatment as outlined in the timetables of Yoder Brothers, Inc., Barberton, Ohio. | |
| Foliage: | | |
| Top side | Dark green, 5GY3/4 | |
| Size | 5" long, 3½" wide | |
| Quantity | Numerous | |
| Shape | Spatulate lobed | |
| Texture | Coarse | |
| Ribs and veins | Moderately prominent | |
| Edge | Moderately indented | |
| Serration | Coarse | |
| Underside | Light green, 5GY5/4 | |
| Stipules | Prominent | |

We claim:

1. A new and distinct cultivar of chrysanthemum characterized particularly as to its uniqueness when compared to the parent cultivar Paragon by its yellow flower color, by its two day earlier response, and by its petal count which is approximately 15% to 25% greater, which contributes to a more highly crowned flower which is more pronounced in the high light periods of the year.

No references cited.

ROBERT E. BAGWILL, Primary Examiner